United States Patent [19]

Pebler et al.

[11] Patent Number: 4,902,402
[45] Date of Patent: Feb. 20, 1990

[54] CHLORIDE CONTAINING SOLID ELECTROLYTE GAS SENSING APPARATUS

[75] Inventors: Alfred R. Pebler, Wilkinsburg; Ching-Yu Lin, Monroeville; Richard P. Kunkle, Irwin, all of Pa.

[73] Assignee: Westinghouse Electric Corp., Pittsburgh, Pa.

[21] Appl. No.: 330,548

[22] Filed: Mar. 30, 1989

[51] Int. Cl.$^4$ .......................................... G01N 27/46
[52] U.S. Cl. .................................. 204/427; 204/1 T; 204/428
[58] Field of Search ................... 204/1 S, 421–429

[56] References Cited

U.S. PATENT DOCUMENTS

| | | | |
|---|---|---|---|
| 3,719,564 | 3/1973 | Lilly et al. | 204/426 |
| 4,377,460 | 3/1983 | Hirayama et al. | 204/195 S |
| 4,427,525 | 1/1984 | Lin et al. | 204/427 |
| 4,492,614 | 1/1985 | Welsh | 204/1 T |
| 4,715,944 | 12/1987 | Yanagida et al. | 204/426 |

*Primary Examiner*—Ta-Hsung Tung
*Attorney, Agent, or Firm*—Daniel P. Cillo

[57] ABSTRACT

A solid NaCl or KCl electrolyte electrochemical concentration cell assembly (20) for measuring monitored gases (38) containing oxygen or a chlorine containing component is divided into two identical alkali ion conductive half cells (22) and (24) where each half cell has solid electrolyte (23) and (25) that consists essentially of NaCl, KCl, or their mixture and is secured to opposite surfaces of the closed end of a solid membrane (36) exhibiting sodium or potassium ion conductivity. The membrane (36) effectively isolates the monitored gases (38) contacting one half cell from a reference gas environment (40) contacting the other half cell.

14 Claims, 1 Drawing Sheet

CHLORIDE CONTAINING SOLID ELECTROLYTE GAS SENSING APPARATUS

BACKGROUND OF THE INVENTION

The requirements for monitoring and controlling stack gas pollutants have resulted in the development of solid electrolyte gas sensors having electrolyte compositions uniquely responsive to gaseous pollutants such as $SO_2$, $CO_2$, $NO_2$, HCl and $Cl_2$. U.S. Pat. No. 4,377,460 (Hirayama and Lin) relates to $SO_2$, $NO_2$, and $CO_2$ gas sensor apparatus utilizing $K_2SO_4$ or $Na_2SO_4$ solid electrolyte for $SO_2$ gas detection, $NaNO_3$ solid electrolyte for $NO_2$ gas detection, and $Na_2CO_3$ solid electrolyte for $CO_2$ gas detection. A mullite ($3Al_2O_3 \cdot 2SiO_2$) membrane containing Na or K impurities is utilized between the electrolyte portions of two separated cells. U.S. Pat. No. 4,427,525 (Lin and Hirayama) utilized the same electrolyte materials, but in a dual solid electrolyte cell configuration consisting of two cells, to provide signals indicative of both $O_2$ and either $SO_2$, $NO_2$ or $CO_2$. A doped $ZrO_2$ membrane containing Na or K impurities is utilized, so as to support alkali cation conductivity as well as $O^=$ ion conductivity.

The above-referenced sensors are electrochemical concentration cells which sense the equilibrium of a gas species of interest and generate an EMF signal corresponding to the difference in partial pressure of the gas species across the solid electrolyte sensor. Typically, the solid state sensor includes an ion conductive solid electrolyte with electrodes disposed on its opposite surfaces. The stack gas, or monitored gas environment, contacts a sensing electrode while the opposite electrode serves as a reference electrode.

Conventional solid electrolyte compositions require operating temperatures of between about 600° C. and 900° C. to exhibit the desired ion conductivity to generate a suitable EMF signal. The accuracy of the EMF measurement depends in part on the effective sealing, or isolation, of the reference electrode from the monitored gas environment contacting the sensing electrode of the electrochemical cell. In a different design, U.S. Pat. No. 4,492,614 (Welsh) describes a concentration cell to detect HCl or $Cl_2$ gas, where the solid electrolyte is selected from a group consisting of gas-impermeable $SnCl_2$, $BaCl_2$ or $PbCl_2$. These materials can be doped to improve ion conductivity by addition of KCl. The solid electrolyte separates a sample gas chamber and a reference gas chamber. Instead of using a constant source of $Cl_2$ reference gas, a solid reference material can be used which exhibits a constant chlorine activity, such as chlorides of aluminum, lithium, copper or sodium. This solid material would be contained in the reference gas chamber.

Hydrogen chloride (HCl) gas is generated during the combustion of chloride containing plastic materials, such as polyvinylchloride, polychloroprene, chlorinated rubber, and others in municipal and industrial incinerators. Incinerators, therefore, may need to be equipped with scrubbers to remove acidic gases as well as particulates on which HCl may be adsorbed. Hydrogen chloride is a very reactive gas and, once airborne, dissipates rapidly by secondary reactions in the atmosphere. Residual HCl gas in incinerator effluents should, therefore, be determined close to the source, preferably in the stack of the incinerator. What is needed is a sensor for HCl, which will allow elimination of expensive CaO or $Y_2O_3$ doped $ZrO_2$ membranes. It is a main object of the invention to provide such a sensor.

SUMMARY OF THE INVENTION

Accordingly, the invention resides in a solid electrolyte gas sensor for measuring either oxygen, or a chlorine containing component gas of a monitored gas environment, by generating an electrical signal on the basis of a difference in the partial pressure between the selected component gas of the monitored gas environment at a monitor electrode in contact with the monitored gas environment and solid electrolyte, and a corresponding component gas of a reference gas environment at a reference electrode in contact with the reference gas environment and solid electrolyte, where the reference electrode is isolated from the monitored gas environment, characterized in that both solid electrolytes are selected from the group consisting of NaCl and KCl, and mixtures thereof.

Preferably, the electrolytes and electrodes are separated by a solid membrane of a composition that exhibits sodium ion conductivity, where each electrolyte contacts the solid membrane, which membrane acts to prevent contact of the monitored gas environment with the reference electrode. An apparatus can be used where the solid membrane is a closed and tubular member with each half cell of electrode and electrolyte disposed in contact with either side of the closed end. This provides a relatively simple HCl or $Cl_2$ detector that operates at elevated temperatures and is ideally suited for in-situ monitoring of HCL or $Cl_2$ in hot incinerator effluents. Additionally, it has been found that some Cl sites of the NaCl or KCl electrolyte are substituted for by $O_2$, primarily in the surface layers. Since NaCl and KCl are considerably cheaper than stabilized zirconia, and cheaper to process, the sensor also provides an inexpensive oxygen sensor.

BRIEF DESCRIPTION OF THE DRAWING

In order that the invention can be more clearly understood, convenient embodiments thereof will now be described, by way of example, with reference to the accompanying drawings, in which.

DESCRIPTION OF THE PREFERRED EMBODIMENTS

Figure 1:
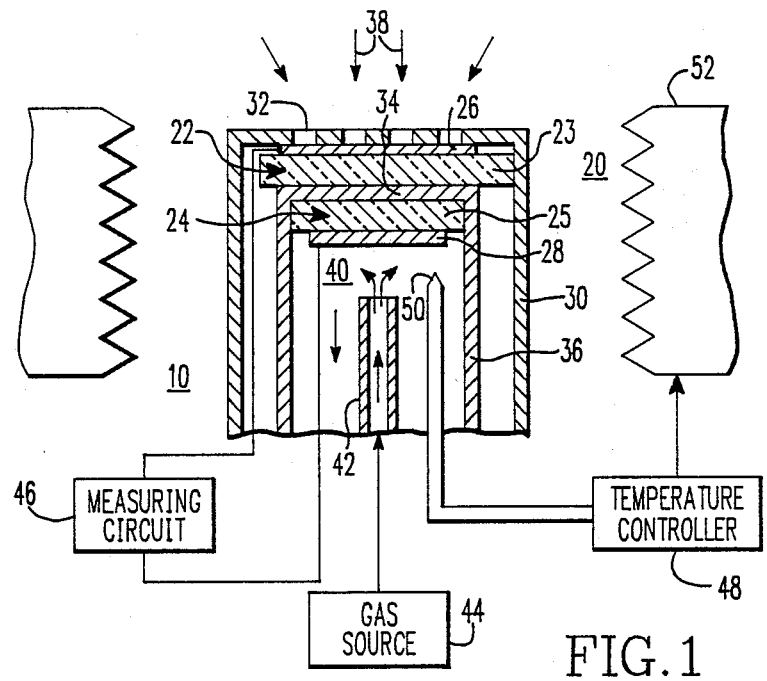
FIG. 1 is an enlarged sectioned illustration of a gas probe assembly incorporating a solid electrolyte electrochemical cell assembly in accordance with the disclosed invention.

Referring now to FIG. 1, the solid electrolyte electrochemical concentration cell assembly 20 shown, consists of identical alkali ion half cells 22 and 24 comprised of solid NaCl or KCl electrolyte element 23 and sensing, metal electrode 26, and solid NaCl or KCl electrolyte element 25 and reference, metal electrode 28 respectively. In all cases, both electrolytes will be of the same composition. In one embodiment, half cells 22 and 24 are secured to opposite surfaces of the closed end 34 of the closed-end tubular membrane 36. The sensing electrode 26, usually platinum, of the electrochemical cell assembly 20 is disposed in contact with a surface of the electrolyte element 23 opposite from the surface contacting the membrane 36. The reference electrode 28, usually platinum, is in intimate contact with the surface of the electrolyte element 25 opposite the electrolyte element surface contacting the membrane 36.

The electrochemical cell assembly 20, consisting of identical alkali ion conductive half cells 22 and 24, is located within the tubular housing 30 having apertures 32 therein to permit the monitored gas environment 38, shown as arrows, containing either oxygen or a chlorine containing component gas, to enter the housing 30 and contact the sensing electrode 26. A reference gas 40, having a stable or known concentration of the gas constituent to be measured, is supplied by an inlet tube 42 from a remote reference gas source 44 for contact with the reference electrode 28. The EMF signal developed by the concentration cell 20 in response to a difference, or change in equilibrium, in the partial pressure of the gas constituent of interest, as measured between the sensing electrode 26 and the reference electrode 28, is manifested by the measuring circuit 46. A temperature controller 48 responds to the electrochemical cell operating temperature as measured by the temperature sensor 50 to control the heater 52 to maintain the operating temperature of the cell 20 essentially constant.

The closed-end tubular membrane 36 can be of a solid composition, i.e. ceramic, glass, etc., exhibiting sodium ion conductivity at elevated temperatures which corresponds to the sodium ion conductivity of the NaCl or KCl electrolyte elements 23 and 25. Experimental evaluation has confirmed that most ceramics incorporate some alkali oxide, such as $K_2O$ and $Na_2O$, in an amount up to a few percent. These ceramic materials become $K^+$ and $Na^+$ ion conductors at elevated temperatures corresponding to the operating temperature of the solid electrolyte electrochemical cell assembly 20.

The combination of a $K^+$ and $Na^+$ ion conductive closed-end tubular membrane 36 with $Na^+$ or $K^+$ ion conductive electrolyte elements 23 and 25 of identical half cells 22 and 24 for monitoring oxygen, HCl or $Cl_2$, provides the required isolation between the monitored gas environment 38 and the reference gas environment RG while supporting the necessary $Na^+$ or $K^+$ ion conduction between the electrodes 26 and 28. Ceramic compositions of beta-alumina ($\beta$-$Al_2O_3$) and beta, double prime-alumina ($\beta''$-$Al_2O_3$) are sodium ion conductors and are suited for use as membrane 36 in combination with NaCl or KCl electrolyte elements 23 and 25, to form electrochemical concentration cells.

While there are numerous solid materials exhibiting alkali oxide content which render them suitable for use as a membrane 36, a preferred membrane material is mullite ($3Al_2O_3 \cdot 2SiO_2$). Mullite is a relatively inexpensive material which not only exhibits $K^+$ and $Na^+$ ion conductivity, but is mechanically strong and capable of extended use at elevated temperatures. Furthermore, mullite is inert to corrosive liquids and gases such as nitric and sulfuric acid which are often present in industrial stack gas environments constituting the monitored gas environment 38.

Sodium chloride and potassium chloride electrolytes have been found to provide the only low cost, useful materials, having ability to monitor not only HCl and $Cl_2$, but also $O_2$. It is essential that the NaCl or KCl be at least 95% pure and preferably have a particle size range before sintering of from 0.5 micrometer to 2.0 micrometers. Within this range sinterability increases, resulting in a pellet that is, advantageously, 95%+ of the theoretical density and which has good electrical conductance. While it is preferred that both electrolyte be either NaCl or KCl, with NaCl being preferred, electrolytes containing a mixture of these two materials are useful. However, when each electrolyte is a mixture of NaCl and KCl components, it is preferred that one of the components should be a major constituent. For example, each electrolyte being 95 wt. % NaCl+5 wt. % KCl, or 95 wt. % KCl+5 wt. % NaCl. The major constituent should constitute at least 95 wt. % of the total electrolyte weight with the rest or remainder being the minor constituent.

The invention will now be illustrated by the following EXAMPLE.

EXAMPLE

A combined $O_2$ and HCl solid electrolyte gas sensor, somewhat similar to that shown in FIG. 1, was constructed using a mullite membrane material to separate two half cells each comprising a platinum gauze electrode, and a solid, pressed 99%+ pure, reagent grade NaCl electrolyte disc 1.27 cm in diameter and 0.95 cm thick made from 0.5 to 2 micrometer NaCl particles. A wax binder was utilized during disc pressing, which was at 352.5 kg./cm² (5,000 psi).

The electrolyte discs were sintered at 700° C. in air for 5 hours. This sintering eliminated all trace of the binder and provided a 95%+ dense electrolyte of good electric conductance. The mullite membrane was in the form of a tube with a flat closed ending, which flat ending served to separate the NaCl half cells and the sample and reference gas compartments of the test cell. In the test cell, the dense NaCl discs were tightly pressed against the flat end of the mullite tube by spring action.

The cell assembly was maintained at 650° C. throughout the test. One portion of a premixed reference gas environment, such as 40 in FIG. 1, containing 1,000 ppm by volume HCl, in air, providing reference circle 1 on the graph of FIG. 2, was passed steadily over the reference electrode. The other portion, such as 38 in FIG. 1, was diluted with air using a rotometer to give gas mixtures containing 750 ppm HCl in air, circle 2 on the graph of FIG. 2; 500 ppm HCl in air, circle 3 on the graph of FIG. 2; 250 ppm HCl in air, circle 4 on the graph of FIG. 2; and 100 ppm HCl in air, circle 5 on the graph of FIG. 2, which were passed over the monitor electrode.

Figure 2:
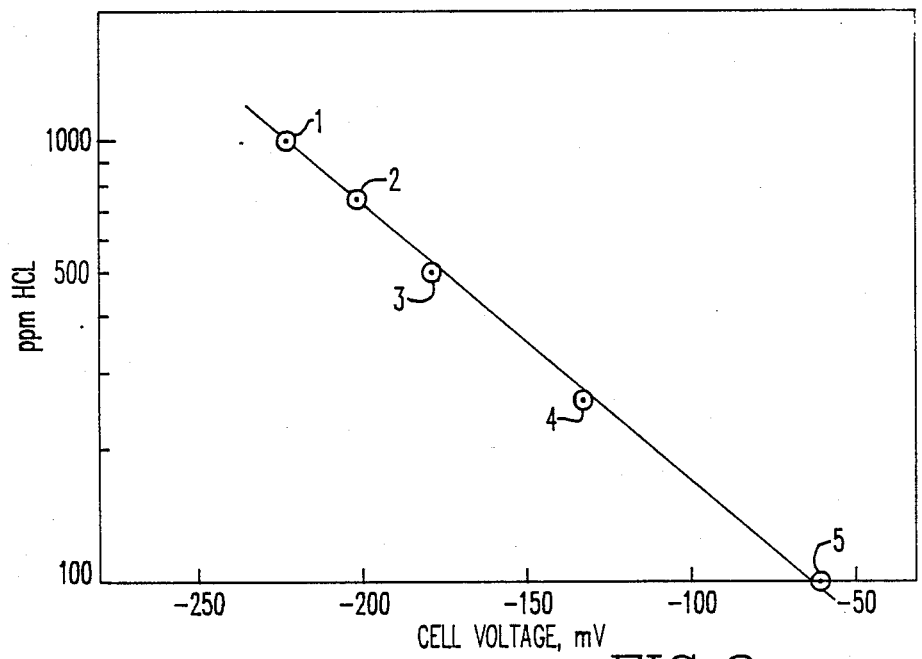
FIG. 2 is a concentration curve for the sensor plotting ppm HCl vs. mV cell voltage.

The calibration curve is shown as FIG. 2. The experimental concentration-voltage data fell on a straight line as would be expected, as the oxygen concentration remains essentially constant. The measured slope of the linear curve (165 mV/decade) is close to the predicted slope (183 mV/decade). In the absence of HCl, this NaCl sensor responds to changes of the oxygen concentration. If HCl gas is added, the cell appears to respond essentially to HCl.

We claim:

1. A solid electrolyte gas sensor for measuring a component gas of a monitored gas environment, by generating an electrical signal on the basis of a difference in the partial pressure between the selected component gas of the monitored gas environment at a monitor electrode in contact with the monitored gas environment and a solid electrolyte, and a corresponding component gas of a reference gas environment at a reference electrode in contact with the reference gas environment and a second solid electrolyte, where the reference electrode is isolated from the monitored gas environment, the improvement characterized in that both solid electrolytes consist essentially of a material selected from the group consisting of NaCl, KCl, and mixtures thereof, both solid electrolytes are of the same composition throughout, at least about 95% dense, and said electrolytes are effective to allow measurement of either an oxygen or chlorine containing component gas.

2. The gas sensor of claim 1, wherein a solid, ion conductive membrane separates the reference electrode and its contacting solid electrolyte from the monitor electrode and its contacting solid electrolyte, where both electrolytes contact the membrane, and where the membrane acts to prevent contact of the monitored gas environment with the reference electrode.

3. The gas sensor of claim 2, wherein the membrane is a closed end tubular member where electrolyte contacts both sides of the closed end.

4. The gas sensor of claim 2, wherein the membrane is a mullite composition and both electrodes are platinum.

5. The gas sensor of claim 1, wherein both solid electrolytes consist of NaCl.

6. The gas sensor of claim 1, wherein both solid electrolytes consist of KCl.

7. The gas sensor of claim 1, wherein both solid electrolytes consists of at least 95 wt. % NaCl, with the remainder being KCl.

8. The gas sensor of claim 1, wherein both solid electrolytes consist of at least 95 wt. % KCl, with the remainder being NaCl.

9. The gas sensor of claim 1, operating in a monitored gas environment containing HCl gas.

10. The gas sensor of claim 1, operating in a monitored gas environment containing $O_2$ but not HCl gas.

11. The gas sensor of claim 1, wherein both electrolytes are made from at least 95% pure powder having a particle size of from 0.5 micrometer to 2.0 micrometers.

12. A solid electrolyte gas sensor for measuring a component gas of a monitored gas environment, by generating an electrical signal on the basis of a difference in the partial pressure between the selected component gas of the monitored gas environment at a monitor electrode in contact with the monitored gas environment and a solid electrolyte, and a corresponding component gas of a reference gas environment at a reference electrode in contact with the reference gas environment and a second solid electrolyte, where the reference electrode is isolated from the monitored gas environment, the improvement characterized in that both solid electrolytes are NaCl, both solid electrolytes are of the same composition throughout, at least 95% pure and at least about 95% dense, and said electrolytes are effective to allow measurement of either an oxygen or a chlorine containing component gas.

13. The gas sensor of claim 12, wherein a solid, ion conductive membrane separates the reference electrode and its contacting solid electrolyte from the monitor electrode and its contacting solid electrolyte, where both electrolytes contact the membrane, and where the membrane acts to prevent contact of the monitored gas environment with the reference electrode.

14. The gas sensor of claim 12 wherein the electrolytes are made from powder having a particle size of from 0.5 micrometer to 2.0 micrometers.

* * * * *